(12) United States Patent
Murooka et al.

(10) Patent No.: US 8,269,160 B2
(45) Date of Patent: Sep. 18, 2012

(54) IMAGE CAPTURING SYSTEM AND IMAGE CAPTURING METHOD

(75) Inventors: Takashi Murooka, Kanagawa (JP); Hideyasu Ishibashi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 472 days.

(21) Appl. No.: 12/606,740

(22) Filed: Oct. 27, 2009

(65) Prior Publication Data

US 2010/0102211 A1    Apr. 29, 2010

(30) Foreign Application Priority Data

Oct. 28, 2008    (JP) .................................. 2008-276877

(51) Int. Cl.
  *A61B 6/00*    (2006.01)
  *G01J 4/00*    (2006.01)
(52) U.S. Cl. ........................................ 250/225; 600/476
(58) Field of Classification Search ................... 250/225; 600/407–476, 310; 356/342, 369, 367, 364
See application file for complete search history.

(56) References Cited

U.S. PATENT DOCUMENTS

| 5,557,324 | A | 9/1996 | Wolff |
| 6,483,585 | B1 * | 11/2002 | Yang .............................. 356/369 |
| 6,772,003 | B2 * | 8/2004 | Kaneko et al. ................ 600/476 |

FOREIGN PATENT DOCUMENTS

| JP | H8-503313 (A) | 4/1996 |
| JP | 2003-47588 (A) | 2/2003 |
| JP | 2006-325973 | 12/2006 |
| JP | 2007-282965 | 11/2007 |

OTHER PUBLICATIONS

Japanese Office Action dated Apr. 17, 2012, with machine English translation.

* cited by examiner

*Primary Examiner* — Tony Ko
(74) *Attorney, Agent, or Firm* — McGinn IP Law Group, PLLC

(57) ABSTRACT

Provided is an image capturing system comprising an irradiating section that sequentially irradiates an observed position with a plurality of types of irradiation light having different polarizations; a polarization filter section that includes a plurality of polarization filter units, which each include a plurality of returned polarized light filters that each pass light having a different polarization, the polarization filter section passing returned light from the observed position having each of the plurality of polarizations; and a light receiving section that receives the returned light passed by the polarization filter section having each of the plurality of polarizations.

20 Claims, 6 Drawing Sheets

IMAGE CAPTURING SYSTEM AND IMAGE CAPTURING METHOD

CROSS REFERENCE TO RELATED APPLICATION

This application claims priority from a Japanese Patent Application No. 2008-276877 filed on Oct. 28, 2008, the contents of which are incorporated herein by reference.

BACKGROUND

1. Technical Field

The present invention relates to an image capturing system and an image capturing method.

2. Related Art

A conventional technique involves selectively switching the wavelength spectrum of light irradiating an observed position, as shown in Japanese Patent Application Publication No. 2007-282965. Another conventional technique involves selectively switching the polarization of light irradiating an observed position, as shown in Japanese Patent Application Publication No. 2006-325973.

With these techniques, however, when a plurality of types of light having different wavelength spectra and polarizations irradiate an observed position, it is impossible to capture a plurality of images in which the returned light from the observed position has different polarization.

SUMMARY

Therefore, it is an object of an aspect of the innovations herein to provide an image capturing system and an image capturing method, which are capable of overcoming the above drawbacks accompanying the related art. The above and other objects can be achieved by combinations described in the independent claims. The dependent claims define further advantageous and exemplary combinations of the innovations herein.

According to a first aspect related to the innovations herein, one exemplary image capturing system may comprise an irradiating section that sequentially irradiates an observed position with a plurality of types of irradiation light having different polarizations; a polarization filter section that includes a plurality of polarization filter units, which each include a plurality of returned polarized light filters that each pass light having a different polarization, the polarization filter section passing returned light from the observed position having each of the plurality of polarizations; and a light receiving section that receives the returned light passed by the polarization filter section having each of the plurality of polarizations.

According to a second aspect related to the innovations herein, one exemplary image capturing method may comprise sequentially irradiating an observed position with a plurality of types of irradiation light having different polarizations; passing returned light from the observed position having each of the plurality of polarizations using a plurality of polarization filter units, which each include a plurality of returned polarized light filters that each pass light having a different polarization; and receiving the returned light passed by the polarization filter units having each of the plurality of polarizations.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention.

Figure 1:
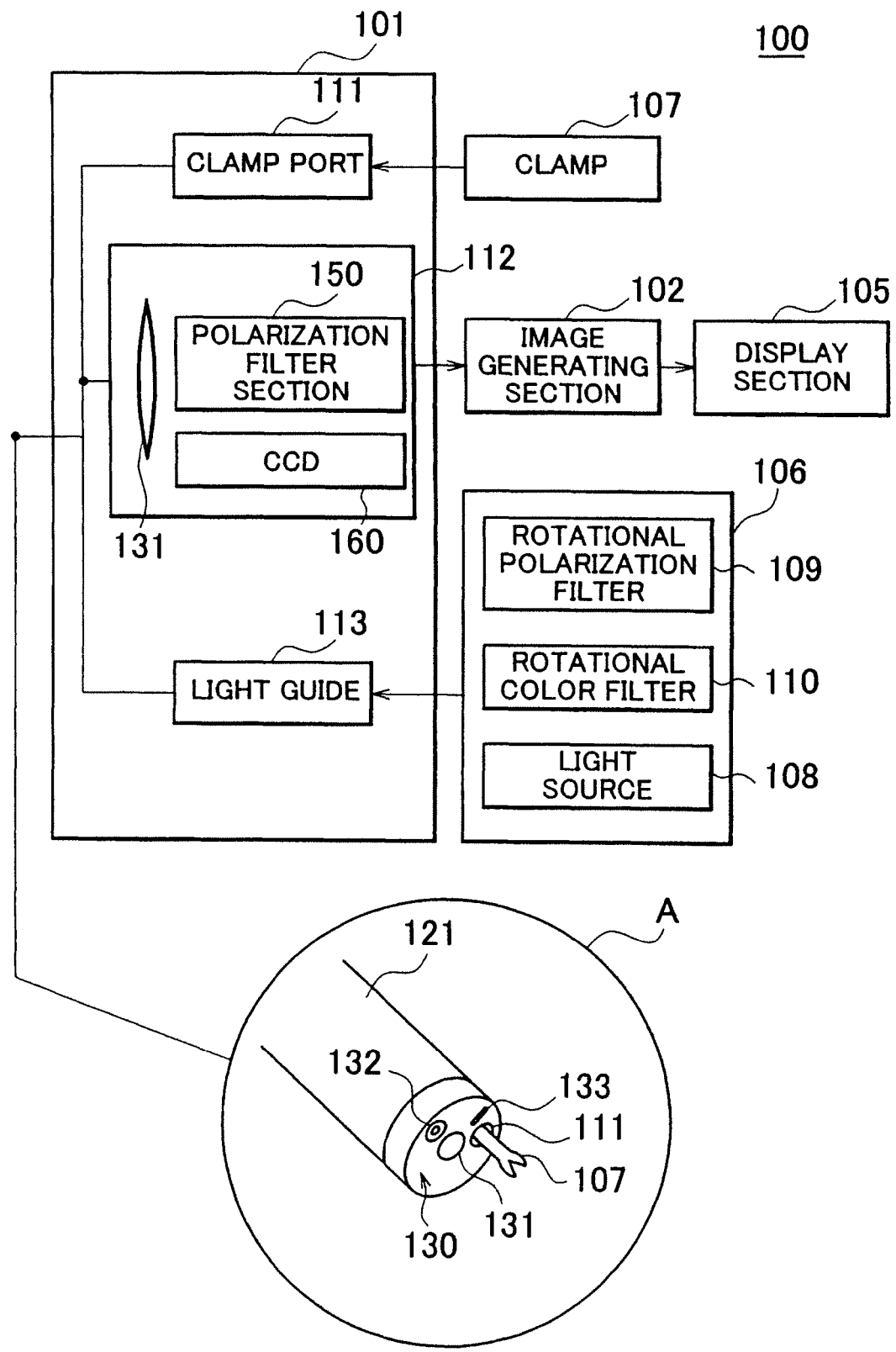
FIG. 1 shows an exemplary configuration of an image capturing system 100 according to an embodiment of the present invention.

FIG. 1 shows an exemplary configuration of an image capturing system 100 according to an embodiment of the present invention. The image capturing system 100 is provided with an endoscope 101, an image generating section 102, a display section 105, an irradiating section 106, and a clamp 107. In FIG. 1, section "A" shows an enlarged view of a tip 121 of the endoscope 101.

The endoscope 101 includes a clamp port 111, an image capturing section 112, and a light guide 113. The tip 121 of the endoscope 101 includes a lens 131 as a portion of the image capturing section 112 on a tip surface 130 thereof. The tip 121 includes an irradiation aperture 132 as a portion of the light guide 113 on the tip surface 130 thereof.

The image capturing section 112 includes a lens 131, a polarization filter section 150, and a CCD 160, which is one example of a light receiving section. Instead of the CCD 160, the image capturing section 112 may include an image capturing element such as a CMOS. The polarization filter section 150 passes, with a plurality of polarizations, the returned light from the observed position that has passed through the lens 131. The CCD 160 receives the returned light having a plurality of polarizations passed by the polarization filter section 150. The image capturing section 112 includes an AD converter, an image capturing elements driver for driving the CCD 160, and the like, but these elements are not shown. In other words, the image captured by the image capturing elements is read by the image capturing element driver and converted into a digital signal by the AD converter.

The irradiating section 106 emits the light that is irradiated from the tip 121 of the endoscope 101. The irradiating section 106 includes a light source 108, and emits the light generated by this light source 108. The light guide 113 transmits light, and may be formed as an optical fiber or the like. The light guide 113 guides the light radiated by the irradiating section 106 to the tip 121 of the endoscope 101. The light radiated by the irradiating section 106 is emitted from the irradiation aperture 132.

The irradiating section 106 sequentially irradiates the observed position with a plurality of types of irradiation light having different polarization states. More specifically, the irradiating section 106 includes a rotational polarization filter 109 and a rotational color filter 110. The rotational color filter 110 includes a plurality of color filters arranged radially throughout the circumference thereof. The rotational polarization filter 109 includes a plurality of irradiation light polarization filters arranged radially throughout the circumference thereof. The plurality of irradiation light polarization filters can include a first polarization filter that that passes irradiation light having a first polarization and a second polarization filter that that passes irradiation light having a second polarization, which is orthogonal to the first polarization. The irradiating section 106 sequentially switches the plurality of color filters by rotating the rotational color filter 110, and sequentially switches the plurality of irradiation light polarization filters by rotating the rotational polarization filter 109. In this way, the irradiating section 106 sequentially irradiates the observed position with a plurality of types of irradiation light having different polarizations, for each different wavelength spectrum.

A clamp 107 is inserted into the clamp port 111, and the clamp port 111 guides the clamp 107 to the tip 121. The clamp 107 may be shaped as any type of tip. In addition to the clamp 107, various other tools for performing processes on an organism may be inserted into the clamp port 111. The nozzle 133 ejects water or air.

The image generating section 102 generates a plurality of images having different polarizations from the image captured by the image capturing section 112. The display section 105 displays the image generated by the image generating section 102.

Figure 2:
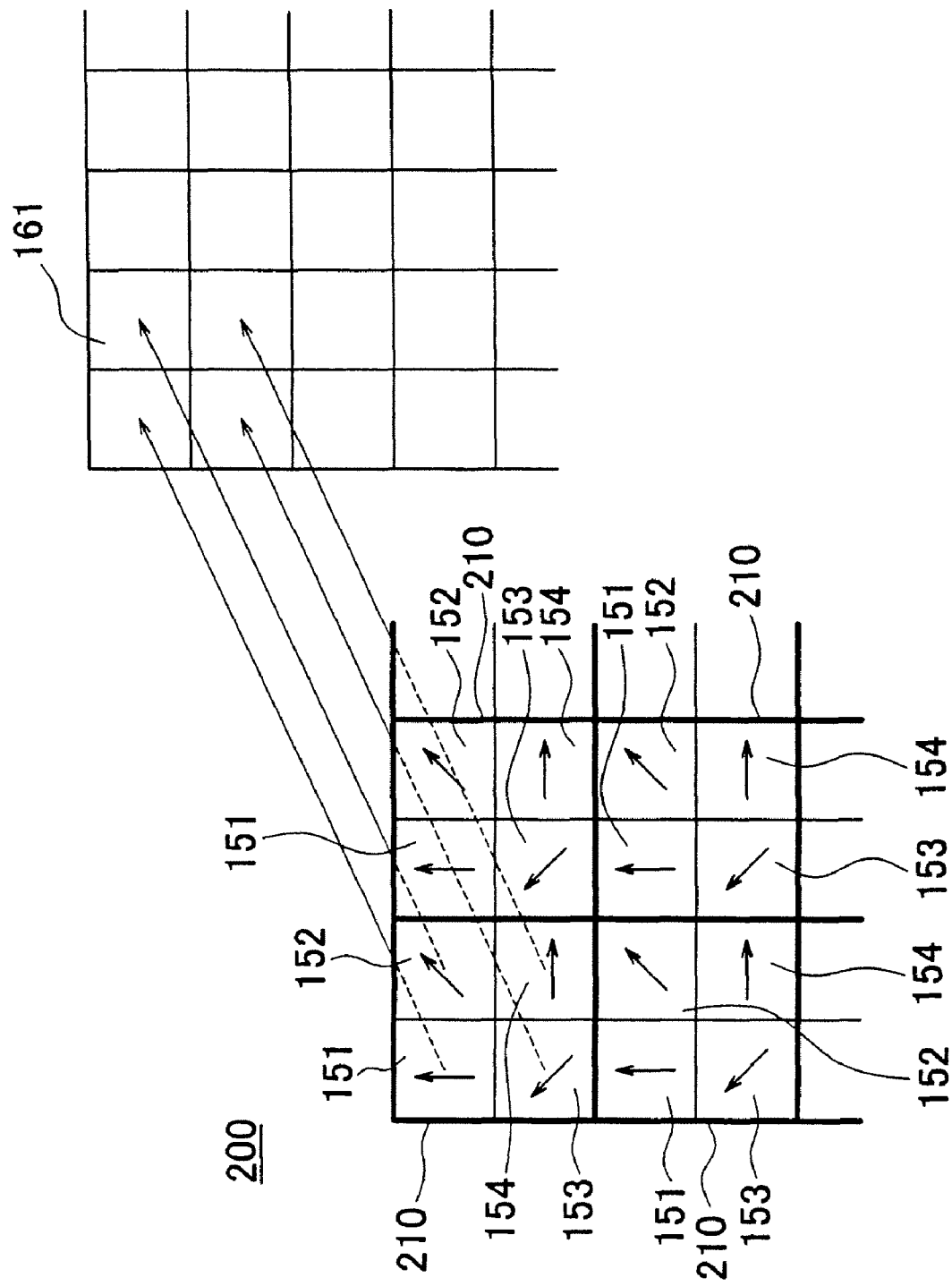
FIG. 2 shows examples of the polarizing plate 200 and the CCD 160 in the polarization filter section 150. The polarizing plate 200 includes a plurality of polarization filter units 210.

FIG. 2 shows examples of the polarizing plate 200 and the CCD 160 in the polarization filter section 150. The polarizing plate 200 includes a plurality of polarization filter units 210. The polarization filter units 210 are arranged in a matrix in the polarizing plate 200.

Each polarization filter unit 210 includes a plurality of returned polarized light filter units that respectively pass a plurality of types of light having different polarizations. More specifically, each polarization filter unit 210 includes a first returned polarized light filter 151, a second returned polarized light filter 152, a third returned polarized light filter 153, and a fourth returned polarized light filter 154 arranged in a matrix. One group of returned polarized light filters from among the plurality of returned polarized light filters may pass a set of light types that are polarized orthogonally to each other.

More specifically, the first returned polarized light filter 151 passes light that is polarized in a first direction. The fourth returned polarized light filter 154 passes light that is polarized in a second direction, which is orthogonal to the first direction. The third returned polarized light filter 153 passes light that is polarized in a third direction, which is not orthogonal to the first direction. The second returned polarized light filter 152 passes light that is polarized in a fourth direction, which is orthogonal to the third direction. In other words, the second returned polarized light filter 152 and the third returned polarized light filter 153 pass light that is polarized in directions different from the first direction and the second direction.

In the example shown in FIG. 2, the first returned polarized light filter 151 passes light that is polarized vertically. The fourth returned polarized light filter 154 passes light that is polarized horizontally. The third returned polarized light filter 153 passes light that is polarized diagonally left. The second returned polarized light filter 152 passes light that is polarized diagonally right.

FIG. 2 shows returned polarized light filters passing light that is linearly polarized, but the returned polarized light filters may instead pass circularly polarized light. Furthermore, FIG. 2 shows returned polarized light filters passing light that is polarized vertically, diagonally left, diagonally right, and horizontally, but the polarized light filters may instead pass light having different polarization directions. Yet further, the number of different polarizations is not limited to four.

The CCD 160 includes a plurality of pixels 161. The pixels 161 correspond one-to-one with the returned polarized light filters 152. In other words, the light passed by a certain returned polarized light filter is received by a single corresponding pixel 161. In this way, the CCD 160 can simultaneously capture a plurality of images having different polarizations. Instead, a certain number n of pixels 161 may correspond to each polarized light filter. In other words, the light passed by a certain polarized light filter may be received by a plurality of corresponding pixels 161.

The image generating section 102 generates images corresponding respectively to each different polarization from the image captured by the image capturing section 112. More specifically, the image generating section 102 generates an image polarized vertically that is captured using light passed by the first returned polarized light filter 151, an image polarized diagonally right that is captured using light passed by the second returned polarized light filter 152, an image polarized diagonally left that is captured using light passed by the third returned polarized light filter 153, and an image polarized horizontally that is captured using light passed by the fourth returned polarized light filter 154.

More specifically, the image generating section 102 generates the image polarized vertically from pixel values of the pixels 161 that capture the image using light passed by the first returned polarized light filter 151. The image generating section 102 generates the image polarized diagonally right from pixel values of the pixels 161 that capture the image using light passed by the second returned polarized light filter 152. The image generating section 102 generates the image polarized diagonally left from pixel values of the pixels 161 that capture the image using light passed by the third returned polarized light filter 153. The image generating section 102 generates the image polarized horizontally from pixel values of the pixels 161 that capture the image using light passed by the fourth returned polarized light filter 154.

The image generating section 102 outputs, to the display section 105, the plurality of images generated with different polarizations. The display section 105 sequentially displays the plurality of images generated by the image generating section 102 having different polarizations. For example, the display section 105 displays, in a predetermined order, the image that is polarized vertically, the image that is polarized diagonally right, the image that is polarized diagonally left, and the image that is polarized horizontally. In this way, the display section 105 can display an image with a shifting polarization. The display section 105 may simultaneously display some or all of the images generated by the image generating section 102 having different polarizations. The display section 105 may be realized as a display apparatus using liquid crystal, organic EL, cathode-ray tubes, plasma, or the like.

The image generating section 102 may realize the above function as a result of a program executed by a CPU of a computer, or as the result of an electronic circuit. The image capturing system 100 may further include a control section that controls each function of the image capturing system 100. In this case, the control section may realize the above function as a result of a program executed by a CPU of a computer, or as the result of an electronic circuit.

Figure 3:
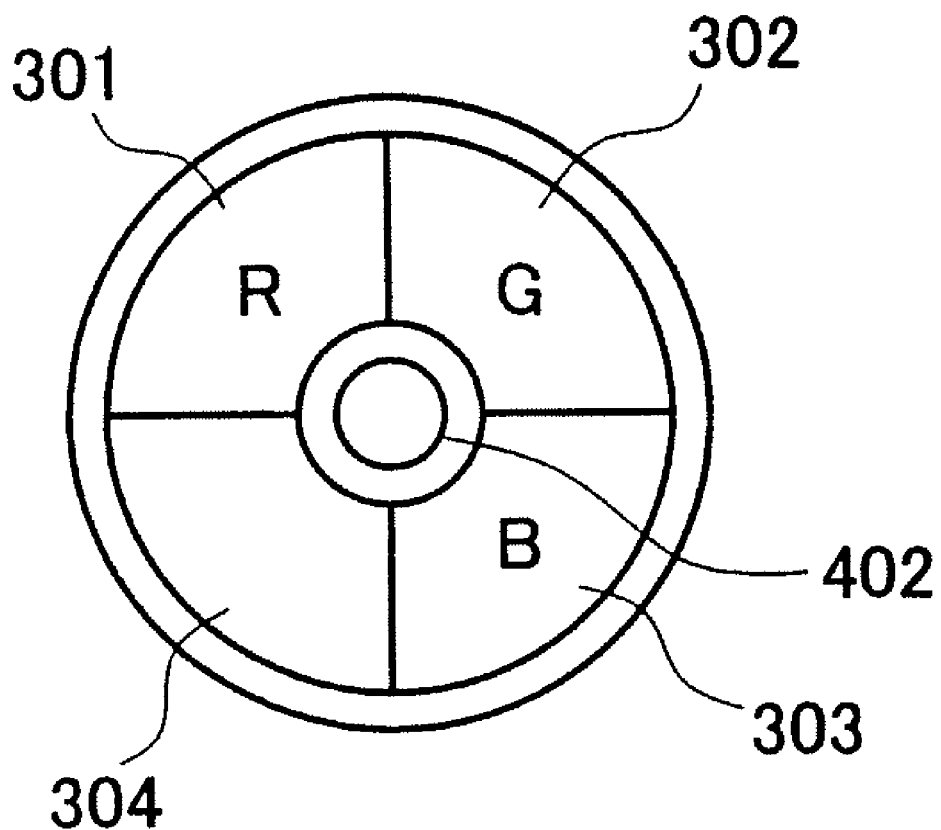
FIG. 3 shows an exemplary rotational color filter 110.

FIG. 3 shows an exemplary rotational color filter 110. The rotational color filter 110 includes a first color filter 301, a second color filter 302, a third color filter 303, and an aperture 304. The first color filter 301 may mainly pass light in a wavelength spectrum whose primary component is in the red wavelength region from 600 to 700 nm, for example. The second color filter 302 may mainly pass light in a wavelength spectrum whose primary component is in the green wavelength region from 500 to 600 nm, for example. The third color filter 303 may mainly pass light in a wavelength spectrum whose primary component is in the blue wavelength region from 400 to 500 nm, for example. The irradiating section 106 can rotate the rotational color filter 110 around an axis 402. Instead of the aperture 304, the rotational color filter 110 may include a color filter that mainly passes light in a wavelength spectrum whose primary component is in the visible light region from 400 to 700 nm, for example.

Figure 4:
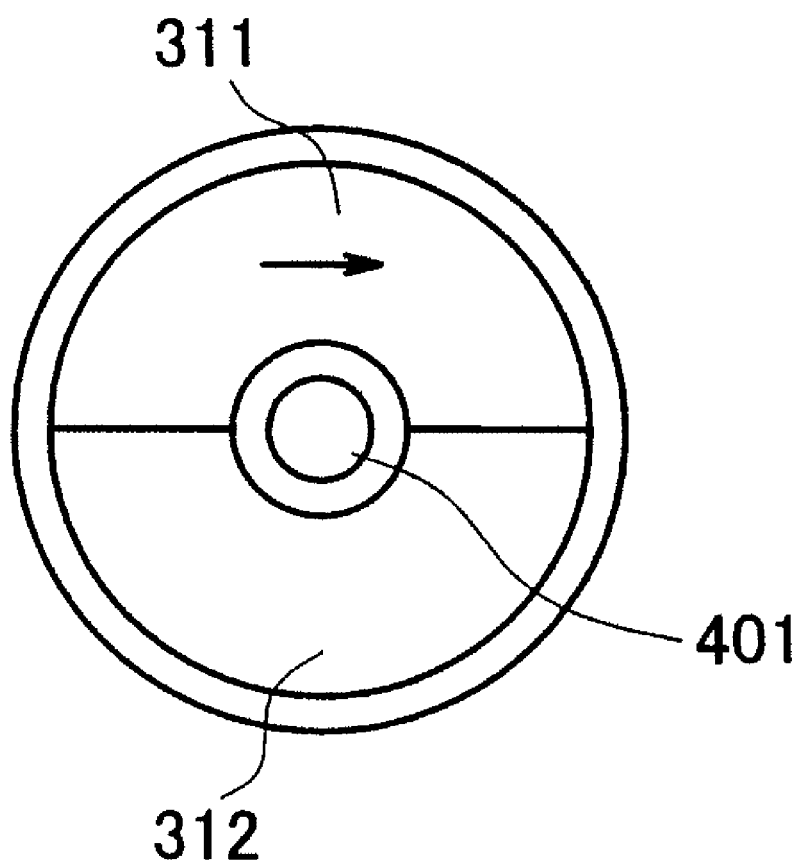
FIG. 4 shows an exemplary rotational polarization filter 109. The rotational polarization filter 109 includes an irradiation light polarization filter 311 and an aperture 312.

FIG. 4 shows an exemplary rotational polarization filter 109. The rotational polarization filter 109 includes an irradiation light polarization filter 311 and an aperture 312. The irradiation light polarization filter 311 passes light that is polarized in a certain direction. The irradiating section 106 can rotate the rotational polarization filter 109 around an axis 401.

Figure 5:
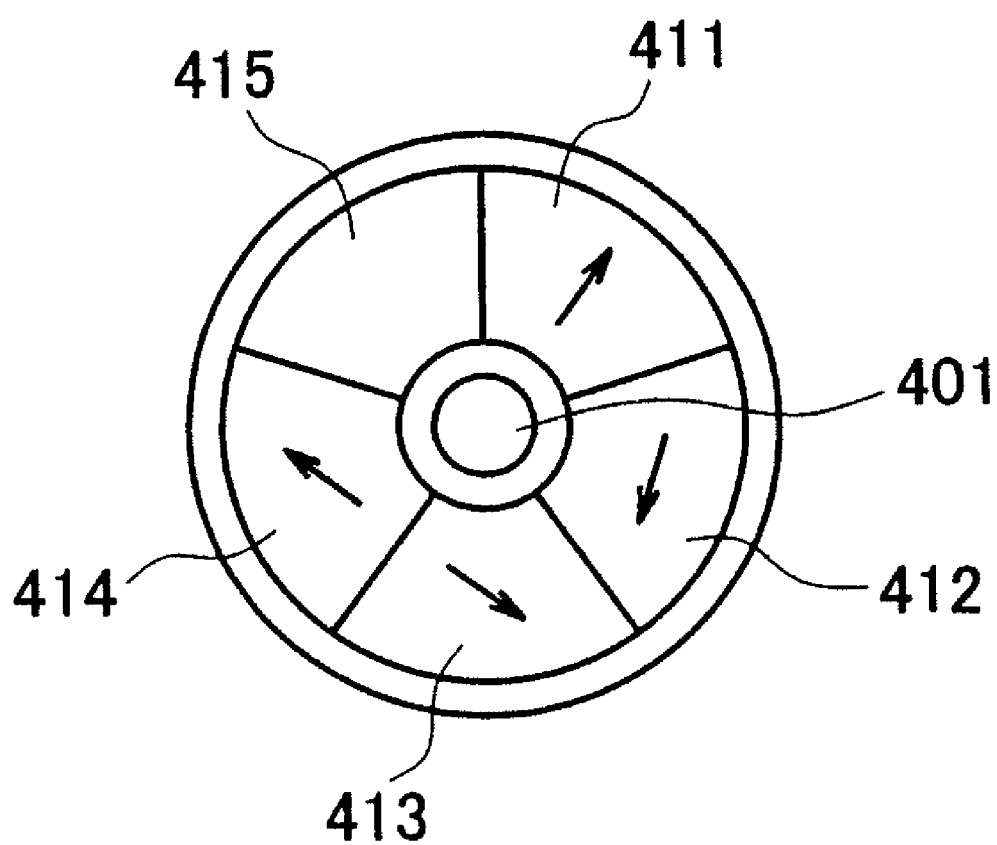
FIG. 5 shows another example of the rotational polarization filter 109.

FIG. 5 shows another example of the rotational polarization filter 109. This rotational polarization filter 109 includes a first irradiation light polarization filter 411, a second irradiation light polarization filter 412, a third irradiation light polarization filter 413, a fourth irradiation light polarization filter 414, and an aperture 415.

The first irradiation light polarization filter 411 passes light that is polarized in a first direction. The second irradiation light polarization filter 412 passes light that is polarized in a second direction, which is orthogonal to the first direction. The third irradiation light polarization filter 413 passes light that is polarized in a third direction, which is not orthogonal to the first direction. The fourth irradiation light polarization filter 414 passes light that is polarized in a fourth direction, which is orthogonal to the third direction. In other words, the third irradiation light polarization filter 413 and the fourth irradiation light polarization filter 414 pass light that is polarized in directions different from the first direction and the second direction.

In the example shown in FIG. 5, the first irradiation light polarization filter 411 passes light that is polarized vertically. The second irradiation light polarization filter 412 passes light that is polarized horizontally. The third irradiation light polarization filter 413 passes light that is polarized diagonally left. The fourth irradiation light polarization filter 414 passes light that is polarized diagonally right. The irradiating section 106 can rotate the rotational polarization filter 109 around the axis 401.

Figure 6:
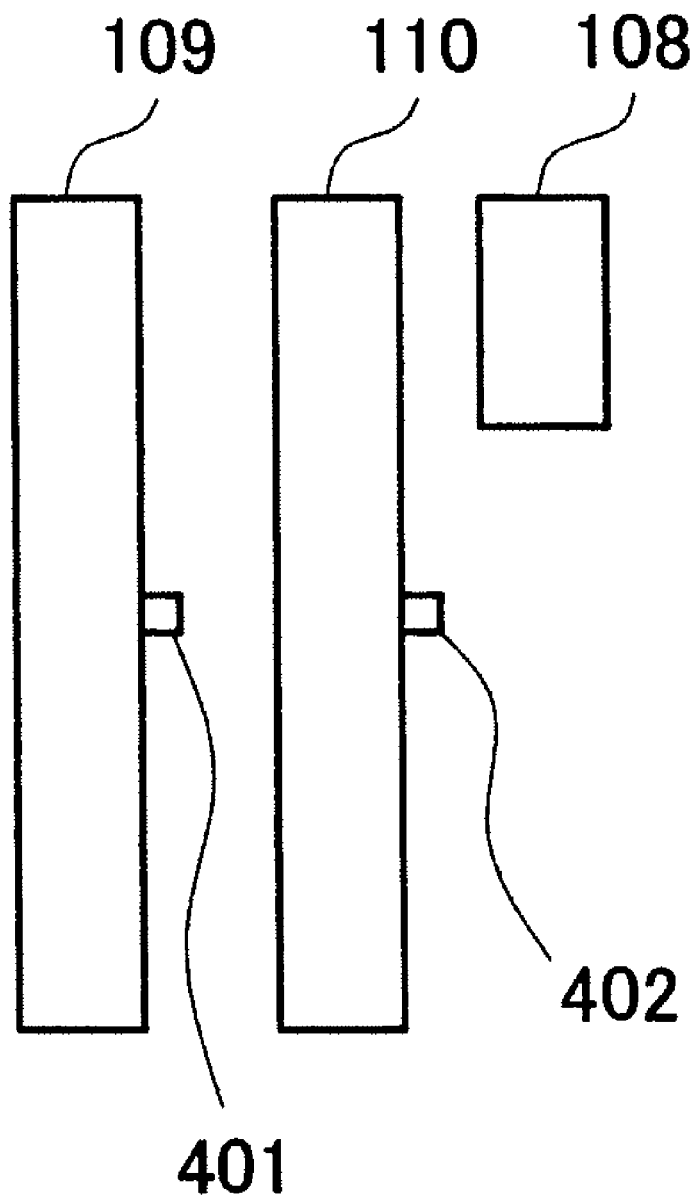
FIG. 6 shows an exemplary correspondence between the rotational polarization filter 109, the rotational color filter 110, and the light source 108.

FIG. 6 shows an exemplary correspondence between the rotational polarization filter 109, the rotational color filter 110, and the light source 108. The irradiating section 106 switches the polarization of the irradiation light emitted from the light source 108 by rotating the rotational polarization filter 109 around the axis 401.

For example, if the irradiating section 106 includes the rotational polarization filter 109 shown in FIG. 5, the irradiating section 106 positions one of the first irradiation light polarization filter 411, the second irradiation light polarization filter 412, the third irradiation light polarization filter 413, the fourth irradiation light polarization filter 414, and the aperture 415 in the optical path of the irradiation light from the light source 108 by rotating the rotational polarization filter 109 around the axis 401. In this way, the irradiating section 106 can irradiate the observed position with light that is polarized vertically, light that is polarized horizontally, light that is polarized diagonally left, light that is polarized diagonally right, and light that is polarized in all directions, resulting from the irradiation light emitted by the light source 108.

On the other hand, if the irradiating section 106 includes the rotational polarization filter 109 shown in FIG. 4, the irradiating section 106 positions one of the irradiation light polarization filter 311 and the aperture 312 in the optical path of the irradiation light from the light source 108 by rotating the rotational polarization filter 109 around the axis 401. In this way, the irradiating section 106 can irradiate the observed position with light from the light source 108 that is polarized in all directions or polarized in a single direction corresponding to the angle of rotation of the rotational polarization filter 109.

Here, the irradiating section 106 switches the polarization of the irradiation light from the light source 108 by changing the angle of rotation of the rotational polarization filter 109 within a range for positioning the irradiation light polarization filter 311 in the optical path described above. For example, if the rotational polarization filter 109 shown in FIG. 4 is used, the irradiation light polarization filter 311 passes irradiation light that is polarized horizontally from among the irradiation light emitted by the light source 108. When the rotational polarization filter 109 is rotated counter-clockwise by substantially 45 degrees from this state, the irradiation light polarization filter 311 passes irradiation light that is polarized diagonally right from among the irradiation light emitted by the light source 108. When the rotational polarization filter 109 is rotated counter-clockwise by substantially 90 degrees from the original state, the irradiation light polarization filter 311 passes irradiation light that is polarized vertically from among the irradiation light emitted by the light source 108. When the rotational polarization filter 109 is rotated counter-clockwise by substantially 135 degrees from the original state, the irradiation light polarization filter 311 passes irradiation light that is polarized diagonally left from among the irradiation light emitted by the light source 108.

The irradiating section 106 switches the wavelength spectrum of the irradiation light emitted from the light source 108 by rotating the rotational color filter 110 around the axis 402. For example, if the irradiating section 106 includes the rotational color filter 110 shown in FIG. 3, the irradiating section 106 positions one of the first color filter 301, the second color filter 302, the third color filter 303, and the aperture 304 in the optical path of the irradiation light from the light source 108 by rotating the rotational color filter 110 around the axis 402. In this way, the irradiating section 106 can switch the wavelength spectrum of the irradiation light emitted by the light source 108.

By rotating the rotational color filter 110 and the rotational polarization filter 109 to sequentially switch through the color filters and the irradiation light polarization filters, the irradiating section 106 can sequentially irradiate the observed position with a plurality of different types of radiation light corresponding to the different polarizations and different wavelength spectra. In this way, the image capturing section 112 can capture a plurality of images using differently polarized returned light from the observed position by capturing each image when the observed position is irradiated with each of the plurality of types of irradiation light having different wavelength spectra and different polarizations.

Here, the irradiating section 106 may sequentially irradiate the observed position with irradiation light resulting from every possible combination of color filters in the rotational color filter 110 and irradiation light polarization filters in the rotational polarization filter 109. Instead, the irradiating section 106 may sequentially irradiate the observed position with irradiation light resulting from a predetermined portion of the possible combinations of color filters in the rotational color filter 110 and irradiation light polarization filters in the rotational polarization filter 109.

For example, if combinations of the color filters in the rotational color filter 110 shown in FIG. 3 and irradiation light polarization filters in the rotational polarization filter 109 shown in FIG. 5 are used, there are 20 different types of irradiation light that can be emitted by the irradiating section 106. The irradiating section 106 may sequentially emit these 20 types of irradiation light. In this case, the image capturing section 112 captures a plurality of images with differently polarized returned light from the observed position, whereby each image is captured respectively when one of the 20 types of irradiation light irradiates the observed position.

The irradiating section 106 may switch, at predetermined intervals, at least one of the color filters in the rotational color filter 110 and the irradiation light polarization filters in the rotational polarization filter 109. For example, the irradiating section 106 may switch at least one of the color filters in the rotational color filter 110 and the irradiation light polarization filters in the rotational polarization filter 109 for each frame or for each set of a prescribed number of frames.

The image capturing system 100 of the present embodiment can obtain a plurality of imagines with differently polarized returned light from the observed position, where each image is captured when the observed position is irradiated with a different combination of a wavelength spectrum and polarization. More specifically, the image capturing system 100 can capture an image having vertically polarized light, an image having horizontally polarized light, an image having diagonally right polarized light, and an image having diagonally left polarized light, and these four types of images are all captured when the observed position is irradiated with each of irradiation light whose primary component is the red wavelength region, irradiation light whose primary component is the green wavelength region, irradiation light whose primary component is the blue wavelength region, and irradiation light whose primary component is the visible light wavelength region. For example, the plurality of images having different polarities that are captured when the observed position is irradiated with irradiation light whose main component is the visible light region may be acquired as black-and-white images in which the observed position is clearly captured.

The image capturing system 100 may generate a composite image or a differential image based on the plurality of images having different polarities that are captured when the observed position is irradiated with irradiation light having one type of waveform spectrum. Instead, the image capturing system 100 may generate a composite image or a differential image based on the plurality of images having the same polarization but captured when the observed position is irradiated with different types of irradiation light. For example, the image capturing system 100 may generate a composite image based on a plurality of images that have the same polarization and that are each captured respectively when the observed position is irradiated with irradiation light whose primary component is the red wavelength region, irradiation light whose primary component is the green wavelength region, and irradiation light whose primary component is the blue wavelength region.

The image capturing system 100 of the present embodiment can obtain a plurality of imagines with differently polarized returned light from the observed position, where each image is captured when the observed position is irradiated with irradiation light having a different polarization. More specifically, the image capturing system 100 can capture an image having vertically polarized light, an image having horizontally polarized light, an image having diagonally right polarized light, and an image having diagonally left polarized light, and these four types of images are all captured when the observed position is irradiated with each of irradiation light that is polarized vertically, irradiation light that is polarized horizontally, irradiation light that is polarized diagonally right, irradiation light that is polarized diagonally left, and polarized light that is polarized in all directions.

For example, the image capturing system 100 of the present embodiment can obtain an image that is polarized horizontally and that is captured when the observed position is irradiated with irradiation light that is polarized vertically, which is an image from which a surface reflection component of the observed position is removed. In particular, the image capturing system 100 of the present embodiment can obtain an image from which the surface reflection component of the observed position is removed for each of the images captured when the observed position is irradiated with irradiation light having the different wavelength spectra.

The image capturing system 100 of the present invention can capture, as an image of the surface reflection component of the observed position, a differential image between (i) the vertically polarized image captured when the observed position is irradiated with vertically polarized irradiation light and (ii) the vertically polarized image captured when the observed position is irradiated with horizontally polarized irradiation light. In particular, the image capturing system 100 of the present embodiment can capture the image of the surface reflection component of the observed position for each of the images captured when the observed position is irradiated with irradiation light having the different wavelength spectra.

The image capturing system 100 may generate a composite image or a differential image based on the plurality of images having the same polarization but captured when the observed position is irradiated with irradiation light having different types of polarization. The image capturing system 100 may generate a composite image or a differential image based on the plurality of images having different polarizations and captured when the observed position is irradiated with irradiation light having a single type of polarization.

The above description used linear polarization as an example of the polarization types of the irradiation light and the returned light, but the polarization type is not limited to linear polarization. Other types of polarization may include circular polarization and elliptical polarization. Further examples may include right-handed circularly polarized light, left-handed circularly polarized light, right-handed elliptically polarized light, and left-handed elliptically polarized light.

More specifically, the irradiation light polarization filters may at least include a polarization filter that passes circularly polarized light or elliptically polarized light. In the same way, the returned polarized light filters may include a returned polarized light filter that passes circularly polarized light or elliptically polarized light. The rotational direction of the polarization surface may be treated in the same way, such that the irradiation light polarization filters at least include a polarization filter that passes right-handed polarized light or left-handed polarized light. In the same way, the returned polarized light filter may include at least a returned polarized light filter that passes right-handed polarized light or left-handed polarized light.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

What is claimed is:

1. An image capturing system comprising:
   an irradiating section that sequentially irradiates an observed position with a plurality of types of irradiation light having different polarizations;
   a polarization filter section that includes a plurality of polarization filter units, which each include a plurality of returned polarized light filters that each pass light having a different polarization, the polarization filter section passing returned light from the observed position having each of the plurality of polarizations; and
   a light receiving section that receives the returned light passed by the polarization filter section having each of the plurality of polarizations.

2. The image capturing system according to claim 1, wherein
   the irradiating section includes a plurality of irradiation light polarization filters that each pass irradiation light having a different polarization, and
   the irradiating section sequentially irradiates the observed position with all of the plurality of types of irradiation light having different polarizations, for each of a plurality of different waveform spectra.

3. The image capturing system according to claim 2, wherein
   the irradiating section includes a rotational polarization filter having the plurality of irradiation light polarization filters arranged radially within the circumference thereof, and
   the irradiating section sequentially switches the plurality of irradiation light polarization filters by rotating the rotational polarization filter.

4. The image capturing system according to claim 2, wherein
   the plurality of irradiation light polarization filters include a first polarization filter that passes irradiation light having a first polarization and a second polarization filter that passes irradiation light having a polarization that is orthogonal to the first polarization.

5. The image capturing system according to claim 4, wherein
   the first polarization filter passes irradiation light polarized in a first direction and the second polarization filter passes irradiation light polarized in a second direction, which is orthogonal to the first direction.

6. The image capturing system according to claim 5, wherein
   the plurality of irradiation light polarization filters further include a third polarization filter that passes irradiation light polarized in a direction that is different from the first direction and the second direction.

7. The image capturing system according to claim 2, wherein
   the plurality of irradiation light polarization filters include at least a polarization filter that passes light having right-handed polarization or left-handed polarization.

8. The image capturing system according to claim 1, wherein
   the polarization filter section includes a polarizing plate in which the plurality of polarization filter units are arranged in a matrix, and
   the polarization filter section uses the polarizing plate to pass returned light from the observed position having each of the plurality of polarizations.

9. The image capturing system according to claim 8, wherein
   the plurality of polarized light filters include a first returned polarized light filter that passes light having a first polarization and a second returned polarized light filter that passes light having a polarization that is orthogonal to the first polarization.

10. The image capturing system according to claim 9, wherein
    the first returned polarized light filter passes light polarized in a first direction, and the second returned polarized light filter passes light polarized in a second direction, which is orthogonal to the first direction.

11. The image capturing system according to claim 10, wherein
    the plurality of returned polarized light filters further include a third returned polarized light filter that passes light polarized in a direction that is different from the first direction and the second direction.

12. The image capturing system according to claim 8, wherein
    the plurality of returned polarized light filters include at least a returned polarized light filter that passes light having right-handed polarization or left-handed polarization.

13. The image capturing system according to claim 1, wherein
    the irradiating section includes:
      a light source;
      a plurality of color filters that each pass a different wavelength spectrum; and
      a plurality of irradiation light polarization filters that each pass irradiation light having a different polarization, and
    the irradiating section sequentially irradiates the observed position with the plurality of types of irradiation light having different polarizations, for each different wavelength spectrum, by sequentially switching the plurality of color filters and the plurality of irradiation light polarization filters.

14. The image capturing system according to claim 13, wherein
    the irradiating section includes:
      a rotational color filter having the plurality of color filters arranged radially within the circumference thereof; and
      a rotational polarization filter having the plurality of irradiation light polarization filters arranged radially within the circumference thereof, and
    the irradiating section sequentially switches the plurality of color filters by rotating the rotational color filter, and sequentially switches the plurality of irradiation light polarization filters by rotating the rotational polarization filter.

15. An image capturing method comprising:
   sequentially irradiating an observed position with a plurality of types of irradiation light having different polarizations;
   passing returned light from the observed position having each of the plurality of polarizations using a plurality of polarization filter units, which each include a plurality of returned polarized light filters that each pass light having a different polarization; and
   receiving the returned light passed by the polarization filter units having each of the plurality of polarizations.

16. The image capturing method according to claim 15, wherein
   sequentially irradiating the observed position includes using a plurality of irradiation light polarization filters that each pass irradiation light having a different polarization to sequentially irradiate the observed position with the plurality of types of irradiation light having different polarizations, for each of a plurality of different waveform spectra.

17. The image capturing method according to claim 16, wherein
   sequentially irradiating the observed position includes sequentially switching the plurality of irradiation light polarization filters by rotating a rotational polarization filter that include the irradiation light polarization filter arranged radially within the circumference thereof.

18. The image capturing method according to claim 15, wherein
   sequentially irradiating the observed position includes sequentially irradiating the observed position with the plurality of types of irradiation light having different polarizations, for each of a plurality of different waveform spectra, by sequentially switching a plurality of color filters that each pass a different wavelength spectrum and a plurality of irradiation light polarization filters that each pass irradiation light having one of the plurality of different polarizations.

19. The image capturing method according to claim 18, wherein
   sequentially irradiating the observed position includes (i) sequentially switching the plurality of color filters by rotating a rotational color filter having the color filters arranged radially within the circumference thereof and (ii) sequentially switching the plurality of irradiation light polarization filters by rotating a rotational polarization filter having the irradiation light polarization filters arranged radially within the circumference thereof.

20. The image capturing method according to claim 15, wherein
   passing returned light includes passing the returned light from the observed position having each of the plurality of polarizations using a polarizing plate in which the plurality of polarization filter units are arranged in a matrix.

\* \* \* \* \*